United States Patent [19]

Brennan et al.

[11] Patent Number: 4,797,298

[45] Date of Patent: Jan. 10, 1989

[54] BRANCHED AMIDES OF L-ASPARTYL-D-AMINO ACID DIPEPTIDES

[75] Inventors: Thomas M. Brennan, Mountain View, Calif.; Michael E. Hendrick, Groton, Conn.

[73] Assignee: Pfizer, Inc., New York, N.Y.

[21] Appl. No.: 944,269

[22] Filed: Dec. 18, 1986

Related U.S. Application Data

[60] Continuation-in-part of Ser. No. 496,428, May 20, 1983, which is a division of Ser. No. 201,745, Nov. 5, 1980, Pat. No. 4,411,925, which is a continuation-in-part of Ser. No. 113,800, Jan. 21, 1980, abandoned.

[51] Int. Cl.$^4$ ..................... C07D 339/02; A23L 1/236
[52] U.S. Cl. ..................................... 426/548; 426/548; 549/38
[58] Field of Search ..................... 549/39, 38; 426/548

[56] References Cited

U.S. PATENT DOCUMENTS

| | | | |
|---|---|---|---|
| 3,492,131 | 1/1970 | Schlatter | 260/112.5 |
| 3,798,204 | 3/1974 | Nakajima et al. | 260/112.5 |
| 3,907,766 | 9/1975 | Fujino et al. | 260/112.5 |
| 3,920,626 | 11/1975 | Ariyoshi et al. | 426/548 |
| 3,959,245 | 5/1976 | Nakajima et al. | 260/112.5 |
| 3,971,822 | 7/1976 | Chibata et al. | 260/468 R |
| 4,256,897 | 3/1981 | Vinick | 548/183 |
| 4,399,163 | 8/1983 | Brennan et al. | 530/801 |
| 4,411,925 | 10/1983 | Brennan et al. | 530/801 |

OTHER PUBLICATIONS

Ariyoshi et al., Bull. Chem. Soc., Japan 47, 326 (1974).
Fujino et al., Chem. Pharm. Bull., 24, 2112 (1976).
Myoshi et al., Bull. Chem. Soc., Japan 51, 1433 (1978).

*Primary Examiner*—Alan Siegel
*Attorney, Agent, or Firm*—Connolly and Hutz

[57] ABSTRACT

Amides of L-aspartyl-D-amino acid dipeptides of the formula

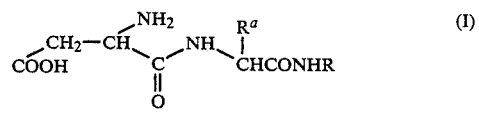

and physiologically acceptable cationic and acid addition salts thereof wherein $R^a$ is methyl, hydroxymethyl, ethyl, n-propyl or isopropyl; R is

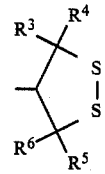

where at least on of $R^3$, $R^4$, $R^5$, $R^6$ is alkyl having from one to four carbon atoms and the remainder are hydrogen or alkyl having from one to four carbon atoms, and the sum of the carbon atoms in $R^3$, $R^4$, $R^5$ and $R^6$ is not greater than six; and when both of $R^3$ and $R^4$ or $R^5$ and $R^6$ are alkyl, they are methyl or ethyl.

Said amides are potent sweeteners having advantages over the prior art, edible compositions containing them, methods for their use in edible compositions and novel amine and amide intermediates useful in their production.

12 Claims, No Drawings

BRANCHED AMIDES OF L-ASPARTYL-D-AMINO ACID DIPEPTIDES

CROSS-REFERENCE TO RELATED APPLICATION

This application is a continuation-in-part of copending application Ser. No. 496,428, filed May 20, 1983, which is a division of Ser. No. 201,745, filed Nov. 5, 1980, now U.S. Pat. No. 4,411,925, which is a continuation-in-part of Ser. No. 113,800, filed Jan. 21, 1980 and now abandoned.

BACKGROUND OF THE INVENTION

The invention relates to novel amides of L-aspartyl-D-alanine, L-aspartyl-D-serine, L-aspartyl-D-2-aminobutyric acid, L-aspartyl-D-valine and L-aspartyl-D-2-aminopentanoic acid which are especially useful in view of their potent sweetening properties, novel methods for their use in foods and edible compositions containing them.

In U.S. Pat. No. 3,492,131 certain lower alkyl esters of L-aspartyl-L-phenylalanine were found to be up to 200 times as sweet as sucrose and to be substantially free of bitter flavor notes which detracted from earlier artificial sweeteners such as saccharin. These compounds were subsequently found to have only limited stability in aqueous systems due to diketopiperazine formation, especially at the neutral-acidic pH conditions prevalent in most food systems, and hydrolysis of the ester group at low pH.

Mazur et al., *J. Med. Chem.*, 16, 1284 (1973) have disclosed that lower alkyl esters of L-aspartyl-D-alanine and certain homologs thereof, especially L-aspartyl-D-alanine isopropyl ester, have sweetness potencies of up to 125 times sucrose.

Sukehiro et al., *Seikatsu Kagaku*, 11, 9–16 (1977); *Chem. Abstr.*, 87, 168407h (1977) have disclosed certain amides of L-aspartyl-D-alanine of the formula

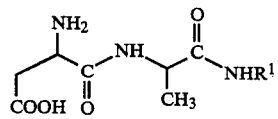

where $R^1$ is methyl, ethyl, n-propyl, isopropyl, n-butyl, isobutyl, secondary butyl, cyclohexyl or the carbon residue of the methyl esters of glycine, d-alanine or l-alanine. The most potent compounds were those wherein $R^1$ is one of the above butyl groups or cyclohexyl, having respectively, 100–125 and 100 times the sweetness of sucrose. Since the n-butylamide was found to have 125 times the sweetness of sucrose and the isobutyl and secondary butyl amides are 100× sucrose, it was concluded that the potency of these amides is affected mainly by the number of carbon atoms in the alkyl group, $R^1$, and that structural isomerism in the alkyl group has little effect on the sweetness potency.

SUMMARY

Unexpectedly, it has now been found that it is not merely the size of the amide substituent that is critical for a high degree of sweetness in L-aspartyl-D-alanine amides, but, to the contrary, it is the precise spatial arrangement of the amide substituent, R, that is critical. It has been found that certain L-aspartyl-D-alanine amides which are branched at the alpha carbon atom (the carbon atom bearing the amide nitrogen atom) and also branched again at one or both of beta and beta' carbon atoms have significant advantages.

Thus, the present invention provides certain novel branched amides of L-aspartyl-D-alanine, L-aspartyl-D-serine and certain other L-aspartyl-D-alpha-alkyl alpha-amino acid dipeptides which have unexpectedly high sweetness potency and are free from undesirable flavor qualities at conventional use levels. They have also been found to have surprisingly high stability both in solid form and in aqueous systems over the pH range found in most food systems even at the elevated temperatures used in baking and conventional food processing.

The novel compounds of the invention are the L-aspartyl-D-amino acid dipeptide amides of the formula

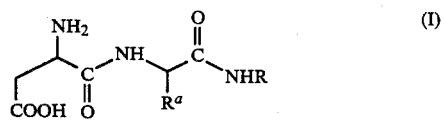

and the physiologically acceptable cationic and acid addition salts thereof, wherein $R^a$ is methyl, hydroxymethyl, ethyl, n-propyl or isopropyl; and R is

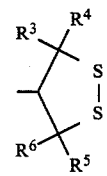

where at least one of $R^3$, $R^4$, $R^5$, $R^6$ is alkyl having from one to four carbon atoms and the remainder are hydrogen or alkyl having from one to four carbon atoms, the sum of the carbon atoms in $R^3$, $R^4$, $R^5$ and $R^6$ is not greater than six and when both of $R^3$ and $R^4$ or $R^5$ and $R^6$ are alkyl, they are methyl or ethyl.

While the preferred sweeteners of the invention are those dipeptide amides of formula (I) wherein the aspartylamino acid dipeptide moiety is derived from L-aspartic acid and a D-amino acid, $R^aCH(NH_2)COOH$, also included within the scope of the invention are mixtures containing the most preferred L-aspartyl-D-amino acid amides of formula (I) wherein one or both of the aspartyl or the other amino acid (i.e., alanine, serine, 2-aminobutyric acid, valine or 2-aminopentanoic acid) moieties is racemic such as e.g., DL-aspartyl-D-alanine amides,
DL-aspartyl-DL-alanine amides,
L-aspartyl-DL-alanine amides,
L-aspartyl-DL-serine amides,
L-aspartyl-DL-valine amides,
DL-aspartyl-DL-2-aminobutyryl amides, and
DL-aspartyl-D-2-aminopentanoic acid amides.

Those compounds of formula (I) wherein the aspartyl moiety is entirely of the D-configuration or the other amino acid moiety is entirely of the L-configuration have little or no sweetness.

An especially preferred group of L-aspartyl-D-amino acid amides of formula (I) are those wherein $R^3$, $R^4$, $R^5$ and $R^6$ are each methyl.

Particularly preferred amides of formula (I) are the L-aspartyl-D-alanine amides, i.e., those wherein $R^a$ is methyl.

An especially valuable sweetener compound of the invention is alpha-L-aspartyl-3,3,5,5-tetramethyl-4-(1,2-dithiolanyl)-D-alanineamide.

The invention further provides compositions for sweetening edible materials which comprises a sweetening amount of a compound of formula (I) and a nontoxic carrier. Most particularly preferred compositions are those containing alpha-L-aspartyl-3,3,5,5-tetramethyl-4-(1,2-dithiolanyl)-D-alanineamide.

Additionally, sweetened edible compositions comprising an edible material and a sweetening amount of a compound of the invention, are provided.

Also provided is a method for sweetening edible compositions which comprises adding thereto a sweetening amount of a compound of the invention.

By physiologically acceptable cationic salts of the compounds of the invention is meant the salts formed by neutralization of the free carboxylic acid group of the compounds of formula (I) by bases of physiologically acceptable metals, ammonia and amines. Examples of such metals are sodium, potassium, calcium and magnesium. Examples of such amines are N-methylglucamine and ethanolamine.

By the term physiologically acceptable acid addition salts is meant those salts formed between the free amino group of the compound of formula (I) and a physiologically acceptable acid. Examples of such acids are acetic, benzoic, hydrobromic, hydrochloric, citric, fumaric, gluconic, lactic, maleic, malic, nitric, phosphoric, saccharic, succinic and tartaric acids.

The invention still further provides novel intermediate amines of the formula

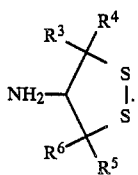

Further valuable novel intermediates, useful in preparation of the invention compounds, are the D-amino acid amides of the formula

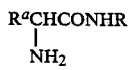

where $R^a$ and R are as previously defined.

DETAILED DESCRIPTION OF THE INVENTION

The instant dipeptide amides are conveniently manufactured by methods suitable for coupling of amino acids. A useful method for preparing the dipeptide amides of formula (I) is outlined below.

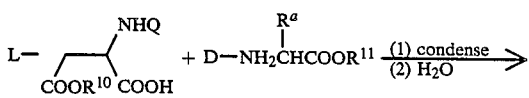

or carboxyl activated derivative

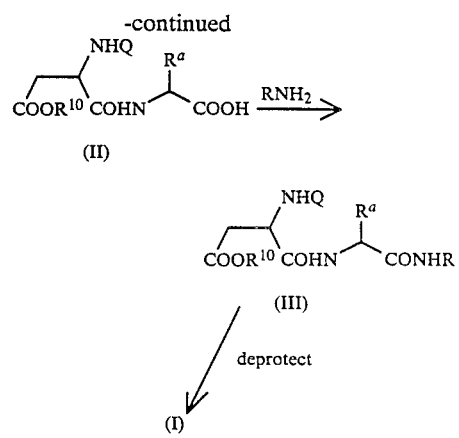

In the above L-aspartic acid derivatives Q is one of the well known amino-protecting groups which can be selectively removed such as those described by Boissonnas, *Advances in Organic Chem.*, 3, 159–190 (1963). Particularly preferred amino-protecting groups are benzyloxycarbonyl and tert-butyloxycarbonyl. $R^{10}$ is preferably an alkyl group having from one to four carbon atoms or benzyl. The D-alanine, D-2-aminobutyric acid, Dvaline or D-2-aminopentanoic acid employed may be in the form of the free amino acid wherein $R^{11}$ is hydrogen, but is preferably a carboxyl-protected derivative wherein $R^{11}$ may be the residue of an ester group such as methyl or ethyl, but is preferably a silyl group such as trialkylsilyl, having from three to twelve carbon atoms. An especially preferred such group is trimethylsilyl for reasons of economy and efficiency.

In the first step of the above reaction sequence the diprotected L-aspartic acid is condensed with the appropriate D-amino acid or a carboxy-protected derivative to provide the diprotected dipeptide of formula (II). While this step may be carried out with the diprotected aspartic acid in the presence of condensing agents such as, for example, dicyclohexylcarbodiimide, it is preferred to employ an alphacarboxyl activated derivative of the diprotected aspartic acid. Preferred such carboxyl activated derivatives are the chloride, bromide, anhydride or mixed anhydride. Especially preferred for reasons of efficiency are the mixed anhydrides of the above diprotected-L-aspartic acids with esters of chlorocarbonic acid, particularly the alkyl esters wherein said alkyl has from one to four carbon atoms. Most preferred mixed anhydrides are those prepared from the methyl and ethyl esters of chlorocarbonic acid for reasons of economy.

In one preferred method for preparing the compounds of formula (I), beta-t-butyl-N-t-butoxycarbonyl-L-aspartic acid is reacted with ethyl chlorocarbonate to form the corresponding mixed anhydride by methods known in the art. In a separate vessel the D-amino acid, $R^aCH(NH_2)COOH$, which is obtained from commercial sources or by resolution of the racemic amino acid by known methods [see e.g. Yamada et al., *J. Org. Chem.*, 38, 4408 (1973)], is converted to the trimethylsilyl ester by contacting the amino acid with an equimolar amount of trimethylsilyl chloride in the presence of a reaction inert organic solvent. Suitable solvents for this purpose are, for example, pyridine, dimethylformamide or dimethylacetamide; especially preferred is dimethylformamide.

In a typical reaction according to this method, the D-amino acid e.g., D-alanine, dissolved in dimethylformamide and an equimolar amount of trimethylchlorosilane is added at room temperature. In a separate flask beta-t-butyl-N-t-butoxycarbonyl-L-aspartic acid and a molar excess of an acid binding agent, preferably triethylamine are dissolved a mixture of dimethylformamide and tetrahydrofuran and an equimolar amount of ethylchlorocarbonate is added at room temperature or below, preferably at about −25° to 25° C. and especially at about −10° to 0° C. to form the mixed anhydride. To this is added the solution of e.g., D-alanine trimethylsilyl ester, preferably at a temperature within the same range. Reaction is ordinarily complete within one to two hours after which the reaction mixture is poured into water or aqueous acid, for example hydrochloric acid, and the product of formula (II) extracted with a water immiscible solvent, typically chloroform, methylene chloride or ethyl ether and isolated by standard methods. The diblocked dipeptide (II) is ordinarily of sufficient purity for use in the next step, but may be further purified if desired, for example by column chromatography.

In the second step of this method the diblocked dipeptide (II) is reacted with an equimolar amount of primary amine of formula $RNH_2$ to provide the corresponding diblocked dipeptide amide intermediate of formula (III) wherein $R^a$, R, $R^{10}$ and Q are as previously defined. As in the first step, the carboxylic acid form of the reactant (II) can be successfully employed by use of condensing agents, for example dicyclohexylcarbodiimide to provide the intermediates of formula (II). However, it is preferred to convert the compound of formula (II) to a carboxyl activated derivative, for example the chloride, bromide or mixed anhydride, the latter being preferred. Thus, employing the particularly preferred compound of formula (II) wherein $R^{10}$ is t-butyl and Q is t-butoxycarbonyl, the mixed anhydride is prepared. As above, the preferred mixed anhydrides are those obtained from esters of chlorocarbonic acid and the methyl or ethyl esters thereof are particularly preferred. The mixed anhydrides of compound (II) are prepared employing reactants and conditions described above for the first step of this sequence. In a typical reaction the compound of formula (II) and triethylamine in approximately equimolar amounts are combined in a reaction inert organic solvent, for example tetrahydrofuran, the mixture cooled to about −10° C. and ethylchlorocarbonate added to obtain the mixed anhydride. To this is then added an equimolar amount of the amine of formula $RNH_2$ or a solution thereof, for example in the same reaction inert solvent and at a temperature in the range of from about −50° to 25° C. and preferably at from −35° to −5° C. After the addition of the amine is complete, the reaction mixture is allowed to warm to about room temperature and maintained at this temperature until reaction is substantially complete, ordinarily from about 1 to 20 hours. The desired intermediate of formula (III) is then isolated and purified, if desired, by the same methods described above for compound (II).

In the final step of this method the carboxyl protecting group, and amino protecting group, Q, are removed to provide the desired sweeteners of formula (I).

The method selected for removal of protecting groups from the dipeptide amide of formula (III) will vary depending on a number of factors which will be apparent to those of skill in the art. Two important factors for such selection are the nature of the protecting groups $R^{10}$ and Q, and the nature of the amide substituent, R. For example, when $R^{10}$ is benzyl or alkyl such as t-butyl as defined above, and Q is tert-butyloxycarbonyl and R has any of the values above, it is ordinarily preferred to remove the protecting groups by hydrolysis.

When hydrolysis is selected for removal of one or both of protecting groups $R^{10}$ and Q, any of the well known methods for alkaline hydrolysis or acid hydrolysis of esters and the like may be employed with some success. When blocking groups $R^{10}$ are to be removed by alkaline hydrolysis, especially preferred conditions include the use of at least an equivalent amount of a strong base, for example, sodium hydroxide or potassium hydroxide in the presence of water and a lower alkanol, particularly methanol or ethanol, at or about room temperature. Under these preferred conditions hydrolytic removal of the $R^{10}$ group is ordinarily complete in a few hours or less.

When the amino protecting group Q is tert-butyloxycarbonyl, it is preferred to use acid hydrolysis for its removal. Especially preferred is dilute aqueous hydrochloric acid in the presence of methanol or ethanol and heating the mixture at reflux. Under these conditions hydrolysis is ordinarily complete in a few hours or less.

When $R^{10}$ and Q are the preferred groups, t-butyl and t-butoxycarbonyl, respectively, a preferred method for simultaneous removal of both blocking groups entails saturation of a solution of the diblocked dipeptide amide in a suitable solvent, e.g., ethanol, chloroform or methylene chloride; with anhydrous hydrogen chloride, subjecting the precipitated hydrochloride salt to mild hydrolysis and pH adjustment to precipitate the desired free base of formula (I).

Isolation of the products of formula (I) after removal of protecting groups by any of the above hydrolysis methods employs standard procedures known in the art. For example, after acid hydrolysis the reaction mixture is evaporated to remove solvent, the aqueous residue washed with a water immiscible non-polar solvent, for example, ethyl ether or chloroform after which the aqueous layer is made alkaline and the product extracted with a water-immiscible solvent such as, for example, ethyl acetate and the product obtained by evaporation of solvent. If desired, the product can be further purified, for example, by recrystallization or column chromatography.

A second preferred method for manufacture of the instant compounds of formula (I) is shown below.

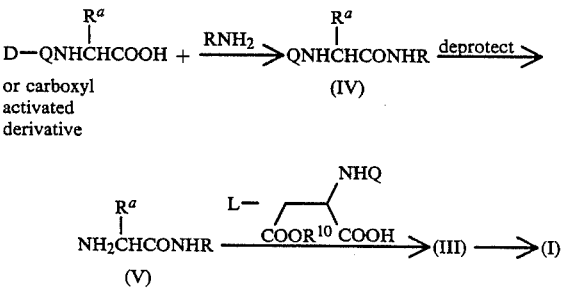

$R^a$, R, $R^{10}$ and Q are as defined above.

The amino protected D-amino acid or its carboxyl activated derivative is reacted with an equimolar amount of amine $RNH_2$ employing methods and conditions described above for the preparation of intermediates (II) and (III) to obtain an amino protected D-amino acid amide of formula (IV). The protecting group Q is removed by hydrogenolysis, or more preferably, by hydrolysis as described above and the resulting free amino amide (V) is condensed with a diblocked L-aspartic acid derivative or a carboxyl activated derivative thereof, as described above for the preparation of intermediates of formula (II), to provide the diblocked dipeptide amide of formula (III) from which the desired sweetener of formula (I) is obtained as previously described.

In a further preferred method for preparing the compounds of the invention the D-amino acid amide of formula (V), described above, is reacted with an acid addition salt of L-aspartic anhydride or with L-aspartic acid N-thiocarboxyanhydride to provide directly the compounds of formula (I). In carrying out this method the intermediate (V) in a suitable solvent is contacted with an equimolar amount of e.g., L-aspartic acid N-thiocarboxyanhydride at a mildly alkaline pH at a temperature of from about $-25°$ to $10°$ C. to provide the compound of formula (I). The alkaline pH for this reaction is provided by means of a strong base, for example, sodium hydroxide or potassium carbonate. Suitable solvents for this reaction are those that dissolve at least a portion of the reactants under the reaction conditions employed without reacting with either reactant to an appreciable extent and allow the products formed in the reaction to be isolated with relative ease. Examples of such solvents for this reaction are water, tetrahydrofuran, 1,2-dimethoxyethane, diethyleneglycol dimethylether, dimethylsulfoxide, dimethylformamide and combinations thereof; preferred solvents are water, and its mixtures with tetrahydrofuran. A preferred alkaline pH range for this reaction is from about 8 to 10 and a pH of about 9 is especially preferred. An especially preferred temperature is in the range of about $-10°$ to $0°$ C.

Under the preferred conditions mentioned above the reaction is ordinarily complete in one to two hours. The product of formula (I) then isolated by standard methods, for example, the pH of the reaction mixture is adjusted to the isoelectric pH of the product, ordinarily about pH 5.0–5.6, to precipitate the product of formula (I), the bulk of the solvent removed by evaporation or filtration and the crude material slurried with an organic solvent, for example, methanol, ethanol, ethyl ether, ethyl acetate or mixtures thereof. The product of formula (I) is then isolated, by filtration for example. It may be further purified, if desired, by, e.g., recrystallization or column chromatography.

The sweetness potency of the instant compounds is determined by comparison of their gustatory sweetnesses with sucrose. Aqueous solutions of the compound of formula (I) diluted to a suitable range of concentrations are compared with a sucrose standard by an expert taste panel. Comparisons are generally made with aqueous sucrose solutions of 7-9%, i.e., 7-9 g. per 100 ml. Higher sucrose concentrations have a distinctive mouthfeel which may influence results and lower sucrose concentration are not indicative of normal use situations. If, for example a 0.014% solution of the compound of formula (I) is judged to be equally as sweet as a 7% sucrose solution, then the sweetness potency of that compound is $7/0.01 = 500 \times$ sucrose. All of the sweetness potency values for the compounds of the invention are determined by this method. At threshold concentrations (i.e., the lowest concentration at which sweetness is first noticed, which for sucrose is ordinarily at concentrations in the range of 2-3%), the potency of a sweetener, such as the compounds of the invention, is generally twice that observed by comparison of its gustatory sweetness with 7-9% solutions of sucrose.

The requisite amines of formula $RNH_2$ wherein R is as previously defined are obtained from readily available precursors. For example, the amines are obtained by reductive amination of the corresponding ketone using a variety of conditions known in the art. For example, reductive amination by the well known Leuckhart reaction employing formic acid and formamide as reducing agents, see for example, the review in *Organic Reactions*, Wiley and Sons, New York, Vol. 5, p. 301, 1949, may be employed. Alternatively, the appropriate ketone can be reductively aminated employing sodium cyanoborohydride and ammonium acetate, see for example, *J. Amer. Chem. Soc.*, 93, 2897 (1971), or by means of ethanolic ammonia in the presence of a hydrogenation catalyst such as Raney nickel, platinum or palladium, see, for example, *Organic Reactions*, 4, 174 (1948). Many of the amines of formula $RNH_2$ are obtained from the corresponding ketones by formation of an intermediate oxime formed by reacting the ketone with hydroxylamine or its salts under conditions well known in the art. The oxime intermediate is then reduced by catalytic hydrogenation or by means of sodium in the presence of a lower alkanol at elevated temperature. One method, especially useful for reducing oximes of sulfur-containing ketones, employs reduction of the oxime in ethanol and a molar excess of sodium at the reflux temperature of the mixture.

An especially preferred method for preparation of the 3- and/or 5-substituted-4-amino-1,2-dithiolane intermediates of the invention employs reaction of the corresponding ketone with titanium tetrachloride in a reaction inert organic solvent, subsequent addition of dry ammonia and reduction with borane in tetrahydrofuran.

The requisite ketone precursors of the amines $RNH_2$ are prepared by known methods. For example, the ketones of formula

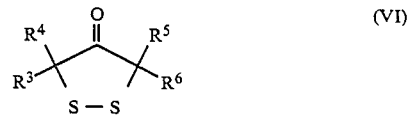

where $R^3$, $R^4$, $R^5$, $R^6$, are as defined above may be obtained by alkylation of the corresponding compounds (VI) wherein $R^3$, $R^4$, $R^5$ and $R^6$ are each hydrogen to provide ketones wherein from one to all of $R^3$, $R^4$, $R^5$, $R^6$ are alkyl as defined above. The alkylation is carried out, for example, employing alkylating agents such as the appropriate alkyl halide or alkyl sulfate under neutral or alkaline conditions provided by strong bases, for example, sodium hydride or sodium amide. Using the same method compounds of the formula (VI) wherein only 1, 2 or 3 of the substituents alpha to the keto group are alkyl can be converted to compounds of the same formula wherein from two to four of $R^3$, $R^4$, $R^5$, $R^6$ are alkyl. Gem-dialkyl ketones of formula (VI) wherein either $R^3$ and $R^4$ or $R^5$ and $R^6$ are said alkyl can be obtained from the appropriate monoalkyl compound by blocking the unsubstituted alpha-position prior to alkylation and subsequent removal of the blocking group. For example, 2,2-dimethyl-1,2-dithiolane-4-one may be obtained by condensation of 2-methyl-1,2-dithiolane- 4-one with ethylformate in the presence of sodium methoxide and the resulting intermediate alkylated as outlined below.

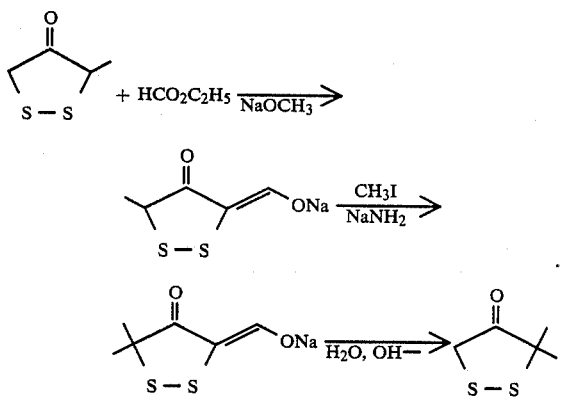

Ketones of formula (VI) wherein one or both of $R^3$ and $R^5$ are propyl or butyl may be obtained by condensation of the corresponding alpha-unsubstituted compound with the appropriate aldehyde or ketone under alkaline conditions to an intermediate alpha- or alpha,alpha'-alkylidene ketone which can then be hydrogenated to provide the desired ketone.

An alternative method for preparing the ketones of formula (VI) involves a cyclization of an acyclic precursor. For example, by means of the well known Dieckmann cyclization of dicarboxylate esters and subsequent hydrolysis and decarboxylation; see e.g., *Modern Synthetic Reactions*, W. A. Benjamin, Menlo Park, Calif., 1972, p. 740. The alpha-keto esters produced, especially those with no other alpha-substituent, can also be alkylated prior to hydrolysis and decarboxylation, if desired. This reaction can also be used to provide ketones (VI) which are unsubstituted at the carbons adjacent to the carbonyl group which can be alkylated as described above.

Certain of the ketones of formula (VI) are also obtained from acyclic precursors derived from ketones of the formula (VIII) w herein $R^3$, $R^4$, $R^5$ and $R^6$ are

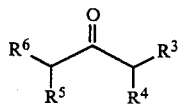 (VII)

as previously defined. In a preferred such method the acyclic ketone (VII) is brominated with two moles of bromine and the resulting alpha,alpha'-dibromo compound cyclized with e.g., a mixture of sodium sulfide and elemental sulfur in dimethylsulfoxide to obtain the desired 4-oxo-1,2-dithiolane (VI) which is isolated by standard extraction and concentration procedures, well known in the art.

The 1,3-dibromoketone derivatives of (VII), described above, also can be converted to the corresponding 1,3-dimercaptoketone by reaction with at least two moles of sodium hydrosulfide. Treating the dimercaptoketone with reagents such as iodine, hydrogen peroxide or hypochlorous acid under disulfide forming conditions, well known in the art provides the ketones of formula (VI)

L-Aspartic acid N-thiocarboxyanhydride is provided in U.S. Pat. Nos. 4,256,897 and 4,321,391, e.g. by reaction of L-aspartic acid sodium salt with methyl ethyl xanthate to provide N-ethoxythiocarbonyl-L-aspartic acid which is reacted with phosphorus tribromide in ethyl acetate to provide the desired product.

The compounds of formula (I) and the physiologically acceptable salts thereof provide advantages as sweetening agents in view of their high potency, their physical form and stability. They are, ordinarily, crystalline, non-hygroscopic, water soluble solids. They are uniquely characterized by possessing a sweet taste, devoid of undesirable harsh or bitter flavor qualities at ordinary use levels. They can be usefully employed to impart sweetness to edible materials. The term "edible materials" as used herein signifies all non-toxic substances consumable by humans or other animals, in solid or liquid form. Illustrative of such substances are: foods, including foodstuffs, prepared food items, chewing gum and beverages; food additives, including flavoring and coloring agents as well as flavor enhancers; and pharmaceutical preparations.

The compounds of the invention can be prepared in a variety of forms suitable for utilization of sweetening agents. Typical forms which can b employed are solid forms such as powders, tablets, granules and dragees; and liquid forms such as solutions, suspensions, syrups, emulsions as well as other commonly employed forms particularly suited for combination with edible materials. These forms can consist of the compounds of formula (I) or their physiologically acceptable salts either apart or in association with non-toxic sweetening agent carriers, i.e. non-toxic substances commonly employed in association with sweetening agents. Such suitable carriers include liquids such as water, ethanol, sorbitol, glycerol, citric acid, corn oil, peanut oil, soybean oil, sesame oil, propylene glycol, corn syrup, maple syrup and liquid paraffin, and solids such as lactose, cellulose, starch, dextrin, modified starches, polysaccharides such as polydextrose (see, e.g. U.S. Pat. Nos. 3,766,165 and 3,876,794), calcium phosphate (mono-, di- or tri-basic) and calcium sulfate.

Likewise useful and compatible are compositions containing a compound of the invention combined with a known sweetening agent such as, for example, sucrose, saccharin, cyclamate, L-aspartyl-L-phenylalanine methyl ester and the like, useful for sweetening edible materials. Especially useful are the mixtures of compounds of formula (I) and saccharin or a physiologically acceptable salt thereof, e.g., the sodium, potassium, calcium or ammonium salt of saccharin. In said mixtures with saccharin the compounds of formula (I) reduce or completely mask the well known, undesirable bitter aftertaste of the saccharin.

The invention also provides sweetened edible compositions comprising an edible material and a sweetening amount of a compound of formula (I), a physiologically acceptable salt thereof alone or in combination with a non-toxic carrier or known sweetening agent. Examples of specific edible materials which provide such sweetened edible compositions include: fruits, vegetables, juices, meat products such as ham, bacon and sausage; egg products, fruit concentrates, gelatins and gelatin-like products such as jams, jellies, preserves, etc.; milk products such as ice cream, sour cream and sherbet; icings, syrups including molasses; corn, wheat, rye, soybean, oat, rice and barley products such as bread, cereals, pasta, cake and cake mixes; fish, cheese and cheese products, nut meats and nut products, beverages such as coffee, tea, carbonated and non-carbonated soft drinks, beers, wines and other liquors; confections such as candy and fruit flavored drops, condiments such as herbs, spices and seasonings, flavor enhancers such as monosodium glutamate and chewing gum. The instant sweeteners are also of use in prepared packaged products such as dietetic sweeteners, liquid sweeteners, granulated flavor mixes which upon reconstitution with water provides non-carbonated drinks, instant pudding mixes, instant coffee and tea, coffee whiteners, malted milk mixes, pet foods, livestock feed, tobacco and consumable toiletries such as mouth washes and toothpaste as well as proprietary and non-proprietary pharmaceutical preparations and other products of the food, pharmaceutical and sundry industries.

Especially preferred sweetened edible compositions are carbonated beverages containing one or more of the instant sweeteners.

The invention is further illustrated by the following examples.

EXAMPLE 1

3,3,5,5-Tetramethyl-1,2-dithiolan-3-one

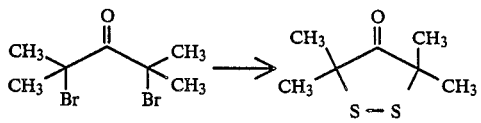

To a solution of 180 g (0.75 mole) sodium sulfide nonahydrate in 2,000 ml dimethylsulfoxide and 300 ml water was added, all at once 24 g (0.75 mole) sulfur. The resulting reddish-black mixture was added over ten minute to a solution of 136 g (0.50 mole) 2,4-dibromo2,4-dimethyl-3-pentanone in 500 ml dimethylsulfoxide. The mixture was allowed to stir at 40°-70° C. for two hours, diluted with five liters of water and the volatile organic compounds removed by steam distillation. The distillate was extracted with ethyl ether, the combined extracts washed with water, brine, dried (MgSO₄) and concentrated to an oil, 106 g. The oil was distilled in vacuo to afford 52.6 g (61%) of the title ketone, b.p. 85°-90° C., 20 mm Hg.
The temperature was allowed to rise to 70° C. during the addition of sodium sulfide. Rapid mechanical stirring was used throughout to ensure complete mixing.

$^1$H-NMR(CDCl₃): 1.3 ppm (singlet).
$^{13}$C-NMR 214.60, 57.74, 25.40.
Infrared spectrum (cm$^{-1}$): 2970, 2924, 2895, 1721, 1460, 1360, 1026.
Mass spectrum (m/e): 176.0 (M+), 144.0, 112.0, 74.0 (base).

EXAMPLE 2

3,3,5,5-Tetramethyl-4-amino-1,2-dithiolane

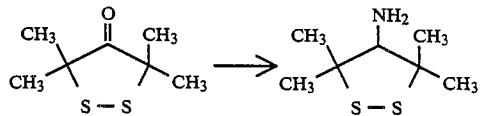

To a 600 ml stainless steel hydrogenation reactor was added 115 ml anhydrous tetrahydrofuran. Dry toluene (5 ml) was added through a clean inlet tube. *The reactor was cooled to 0°-10° C. and a solution of 15 ml (0.14 mole) titanium tetrachloride in 20 ml toluene was added all at once followed by a 5 ml toluene wash. The mixture was stirred at room temperature for 30 minutes. To this was added 10.0 g (0.056 mole) 3,3,5,5-tetramethyl-1,2-dithiolan-4-one followed by two 5 ml toluene washes. The resulting mixture was allowed to warm to 50° C. during the addition. Ammonia gas was bubbled through the mixture for one hour. The reactor was then sealed and heated at 100° C. for 18 hours. After cooling to 40° C., 71 ml (0.071 mole) 1M borane in tetrahydrofuran (BH₃/THF) was added in one portion and the mixture stirred at 40°-50° C. for eight hours. The excess borane was cautiously quenched with 5 ml methanol followed by 10 ml of 1:1 methanol/water. The reaction mixture was added to 500 ml 1M hydrochloric acid, the resulting clear solution washed with ethyl ether (3×500 ml) and the aqueous phase adjusted to pH 12 with 50% (w/v) sodium hydroxide solution. The resulting slurry was triturated with ethyl ether (4×200 ml), the combined ether layers dried (MgSO₄) and solvent evaporated to afford 8.4 g (84%) of the title compound as an oil, b.p. 135°-140° C. at 40 mm Hg.
All additions were made using syringes while the reactor was under a slight vaccum.

$^1$H-NMR(CDCl₃)ppm(delta): 2.65 (s, 1H), 1.4 (s, 6H), 1.28 (s, 6H).
$^{13}$C-NMR(CDCl₃)ppm(delta): 75.1, 59.5, 29.6, 22.6.
Mass spectrum (m/e): 177 (M+), 125, 98, 71 (base).

EXAMPLE 3

N-t-Butoxycarbonyl-3,3,5,5-tetramethyl-4-(1,2-dithiolanyl)-D-alanineamide

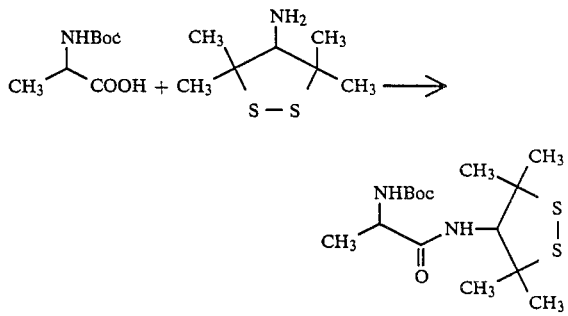

To a solution of 9.01 g (0.047 mole) N-t-butoxycarbonyl-D-alanine and 5.6 ml (0.05 mole) N-methyl morpholine in 50 ml dry tetrahydrofuran at −10° to −15° C., was added slowly over five minutes 4.4 ml (0.047 mole) ethyl chloroformate. The mixture was stirred for 15 minutes, cooled to −20° C. and 8.4 g (0.047 mole) 3,3,5,5-tetramethyl-4-amino-1,2-dithiolane in 10 ml dry tetrahydrofuran was added. The resulting mixture was allowed to warm to room temperature over two hours, diluted with 100 ml water and concentrated in vacuo to 150 ml total volume. The concentrate was extracted with methylene chloride (3×200 ml), the combined extracts washed with 1M hydrochloric acid (2×200 ml), saturated sodium bicarbonate solution (2×200 ml), brine (2×200 ml) and the organic layer dried (MgSO₄) and concentrated in vacuo to afford 8.2 g of crude product as an oil. This was purified by silica gel column chromatography, eluting with chloroform to obtain the title compound as a solid, 6.3 g (38.5%), m.p. 160°-162° C. (decomp.).

$^1$H-NMR(CDCl₃)ppm(delta): 6.54 (br d, 1H), 5.07 (br s, 1H), 4.17 (d, 2H), 1.46 (d, 6H), 1.42 (s, 9H), 1.35 (9H).
$^{13}$C-NMR(CDCl₃)ppm(delta): 172.7, 156.02, 80.67, 69.74, 60.16, 60.08, 50.49, 29.32, 28.35, 24.13, 24.06, 17.35.

EXAMPLE 4

3,3,5,5-Tetramethyl-4-(1,2-dithiolanyl)-D-alanineamide

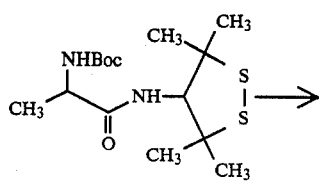

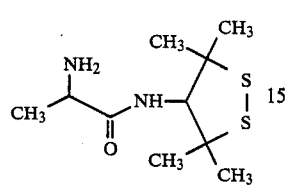

A mixture of 6.0 g (0.17 mole) N-t-butoxycarbonyl-3,3,5,5-tetramethyl-4-(1,2-dithiolanyl)-D-alanineamide, ml concentrated hydrochloric acid, 100 ml 95% ethanol and 30 ml water was heated at reflux for two hours. The mixture was cooled to room temperature, poured into 300 ml 1M hydrochloric acid, washed with 4×500 ml ethyl ether and the aqueous layer adjusted to pH 12 with 50% (w/v) sodium hydroxide solution. The alkaline solution was extracted with chloroform, the combined extracts dried (MgSO4) and concentrated to dryness in vacuo to yield 3.62 g (86%) of the title amide, m.p. 118°–122° C. (decomp.).

EXAMPLE 5

Beta-t-Butyl N-t-butoxycarbonyl-L-aspartyl-3,3,5,5-tetramethyl-4-(1,2-dithiolanyl)-D-alanineamide

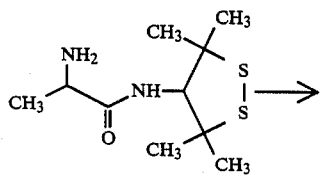

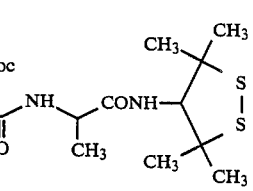

To a solution of 3.5 g (0.012 mole) beta-t-butyl N-t-butoxycarbonyl-L-aspartic acid and 2.19 g (0.02 mole) N-methylmorpholine in 25 ml tetrahydrofuran at −10° to −15° C., was added over five minutes 0.95 ml (0.01 mole) ethyl chloroformate and the resulting mixture stirred for 15 minutes. After cooling to −20° C., 3.0 g (0.012 mole) 3,3,5,5-tetramethyl-4-(1,2-dithiolanyl)-D-alanineamide dissolved in 15 ml dry tetrahydrofuran was added. The mixture was then allowed to warm to room temperature (two hours), diluted with 100 ml water and concentrated to 100 ml total volume. The concentrate was extracted with methylene chloride, washed with 1M hydrochloric acid, saturated sodium bicarbonate, brine, dried (MgSO4) and concentrated in vacuo to an oil, 8.0 g. The oil was purified by silica gel column chromatography by elution with chloroform and chloroform/methanol 9:1 to afford 6.3 g (99%) of the desired diblocked dipeptide amide.

EXAMPLE 6

Alpha-L-Aspartyl-3,3,5,5-tetramethyl-4-(1,2-dithiolanyl)-D-alanineamide

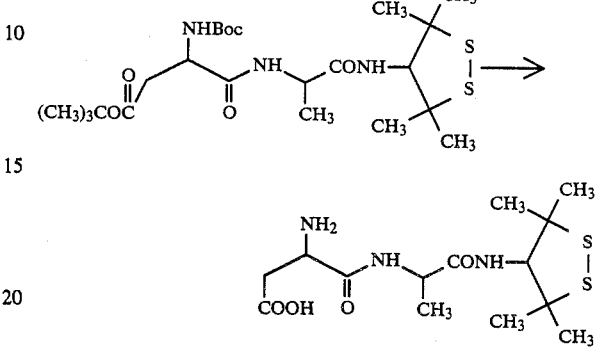

A solution of 1.5 g (0.003 mole) beta-t-butyl N-t-butoxycarbonyl-L-aspartyl-3,3,5,5-tetramethyl-4-(1,2-dithiolanyl)-D-alanineamide in 50 ml ethanol-free chloroform was saturated with hydrogen chloride gas. The resuling slurry was concentrated to obtain 1.04 g (87%) of the desired product as its hydrogen chloride salt. A 0.50 g portion was dissolved in about 3 ml water, adjusted to pH 5.9 with bicarbonate solution and the precipitated free base collected by filtration and air dried to obtain 0.40 g of the title dipeptide amide. Mass Spectrum (M+): 363.1334, Calculated for $C_{14}H_{25}N_3S_2O_4$: 363.1380.

$^1$H-NMR(DMSO-d$_6$)ppm(delta): 8.74 (br s, 1H), 7.8 (d, 1H), 4.65 (br, s, 3H), 4.4 (m, 1H), 4.1 (d, 1H), 3.75 (m, 1H), 2.5 (m, 1H), 2.25 (m, 1H), 1.40 (s, 3H), 1.35 (s, 6H), 1.31 (s, 3H), 1.26 (d, 3H).

$^{13}$C-NMR(DMSO-d$_6$)ppm(delta): 172.89, 182.77, 170.65, 69.43, 59.27, 50.77, 48.58, 38.09, 29.08, 28.94, 23.75, 23.60, 18.57.

EXAMPLE 7

4-Amino-3,5-Dimethyl-1,2-Dithiolane

A. Reaction of sodium sulfide and elemental sulfur in dimethylsulfoxide/water with 2,4-dibromo-3-pentanone by the method of Example 1 affords 3,5-dimethyl-1,2-dithiolan-3-one in like manner.

B. Reductive amination of 3,5-dimethyl-1,2-dithiolan-3-one in the presence of titanium tetrachloride and ammonia by the method of Example 2 affords the desired 4-amino-1,2-dithiolane.

C. In like manner, when the appropriate dibromoketone is reacted with sodium sulfide by the method of Example 1 and the resulting substituted 1,2-dithiolan-3-one subjected to reductive amination by the method of Example 2, the following amines are obtained.

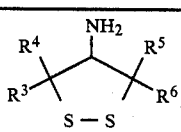

| $R^3$ | $R^4$ | $R^5$ | $R^6$ |
| --- | --- | --- | --- |
| CH$_3$ | H | H | H |
| C$_2$H$_5$ | H | H | H |

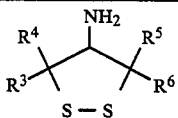

| $R^3$ | $R^4$ | $R^5$ | $R^6$ |
| --- | --- | --- | --- |
| i-C$_3$H$_7$ | H | H | H |
| C$_2$H$_5$ | H | C$_2$H$_5$ | H |
| i-C$_3$H$_7$ | H | i-C$_3$H$_7$ | H |
| i-C$_3$H$_7$ | H | C$_2$H$_5$ | H |
| t-C$_4$H$_9$ | H | CH$_3$ | CH$_3$ |
| C$_2$H$_5$ | CH$_3$ | CH$_3$ | CH$_3$ |

EXAMPLE 8

L-Aspartyl-D-alanine-N-(3,5-dimethyl-1,2-dithiolan-4-yl)amide

A. N-tertiary-butoxycarbonyl-D-alanine

To 7.0 ml each of tetrahydrofuran and water was added 2.71 g (11 mmole) N-(t-butoxycarbonyloxyimino)-2-phenylacetonitrile (BOC-ON, Aldrich Chemical Co.), 0.89 g (10 mmole) D-alanine and 1.5 g (15 mmole) triethylamine and the resulting two phase mixture stirred at room temperature. After about two hours the mixture became homogeneous and stirring was continued overnight. The mixture was diluted with water, washed with ethyl acetate and acidified with dilute hydrochloric acid to pH 1.5. The acidified solution was extracted with ethyl acetate, the extracts washed with water, saturated brine and dried over sodium sulfate. The solvent was evaporated at reduced pressure to afford 1.9 g of product as a colorless oil suitable for use in the next step.

B. N-(3,5-Dimethyl-1,2-dithiolan-4-yl)-t-butoxycarbonyl-D-alanine salt

Under anhydrous conditions, to a mixture of 1.7 g (8.9 mmole) of N-t-Boc-D-alanine obtained in Part A, 1.98 g (19 mmole) triethylamine and 40 ml of tetrahydrofuran, cooled to −10° C. is added dropwise 0.96 g (8.9 mmole) ethyl chloroformate and the resulting mixture is stirred at this temperature for 20 minutes. To this is added 1.1 g (7.5 mmole) of mixed cis- and trans-isomers of 4-amino-3,5-dimethyl-1,2-dithiolane and the resulting mixture is stirred at −10° C. for 10 minutes, then allowed to warm to room temperature. The reaction mixture is diluted with water and extracted with ethyl acetate. The organic layer is washed with sodium bicarbonate solution, dilute hydrochloric acid, water, brine, then dried (Na$_2$SO$_4$) and the solvent is evaporated at reduced pressure to obtain the desired product which is used in the next step.

C. N-(3,5-Dimethyl-1,2-dithiolan-4-yl)-D-alanine amide

The t-Boc-amide obtained in Part B is dissolved in 15 ml of ethanol and a mixture of 5 ml of concentrated hydrochloric acid and 10 ml of water is added. The resulting mixture is heated at reflux for 30 minutes, cooled and the ethanol removed by evaporation in vacuo. The aqueous residue is washed with ethyl ether, made alkaline with sodium hydroxide solution, extracted with ether and the extracts dried (Na$_2$SO$_4$). Evaporation of solvent provides the desired amino acid amide.

D. Coupling of D-alanine amide with L-aspartic acid N-thiocarboxyanhydride

The D-alanine amide provided in Part C, 1.1 g (5.1 mmole) is dissolved in 5 ml of tetrahydrofuran and 5 ml of water is added. The clear solution is cooled in ice and 0.89 g (5.1 mmole) of L-aspartic acid N-thiocarboxyanhydride is added in one portion. To this is added as required, 0.5M sodium hydroxide to maintain the mixture at pH 9. After stirring 30 minutes the reaction mixture is washed with ethyl ether, then ethyl acetate and the washes are discarded. The aqueous phase is acidified with dilute hydrochloric acid to pH 5.6 and evaporated to dryness at reduced pressure. The residue is taken up in hot methanol, filtered and the methanol evaporated. The residue is taken up again in hot methanol, filtered and the filtrate decolorized with activated carbon, filtered through diatomaceous earth and the filtrate is evaporated to obtain the crude product. The crude product is dissolved in hot water and filtered, concentrated under a stream of nitrogen to a small volume and cooled to precipitate the title compound.

Use of D-2-aminobutyric acid, D-serine, D-valine or D-2-aminopentanoic acid in place of D-alanine in the procedure of Part A above and reacting the N-t-butoxycarbonyl-D-amino carbonyl-D-amino acids thus obtained in the procedures of Parts B, C and D, similarly provides the corresponding compounds of formula (I) wherein R is 3,5-dimethyl-1,2-dithiolan-4-yl and R$^a$ is C$_2$H$_5$, CH$_2$OH, (CH$_3$)$_2$CH, or CH$_3$CH$_2$CH$_2$, respectively.

EXAMPLE 9

L-Aspartyl-D-serine N-(3,3,5,5-tetra-methyl-1,2-dithiolan-4-yl) amide

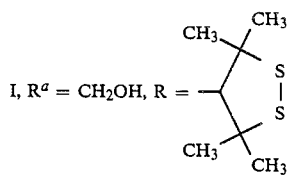

A. 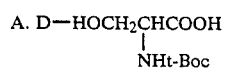

The method is tht described by Moroder et al., Z. Physiol. Chem. 357, 1651 (1976), for preparing t-Boc-amino acids. To 10 ml each of dioxane and water was added 2.18 g (10 mmole) di-t-butyl dicarbonate 1.6 ml (11.5 mmole) triethylamine and 1.05 g (10 mmole) D-serine. The mixture was stirred for 30 minutes at room temperature and the dioxane evaporated in vacuo. The aqueous residue was cooled in ice, ethyl acetate was added and the mixture stirred while adding dilute potassium bisulfate solution to pH 2–3. The aqueous layer was separated, extracted twice with ethyl acetate and the combined extracts washed with water, dried (Na$_2$SO$_4$) and the solvent evaporated in vacuo to yield 1.7 g of product as a viscous paste.

B. 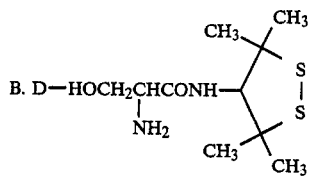

A mixed anhydride was prepared from 2.85 g (14 mmole) of N-t-butoxycarbonyl-D-serine, 1.55 ml N-methylmorpholine, 1.34 ml ethyl chloroformate in 75 ml methylene chloride at −12° to −10° C. by the method of Example 3. To this mixture was added 2.48 g (14 mmole) of 4-amino-3,3,5,5-tetramethyl-1,2-dithiolane and stirring continued for five minutes at -12° C. The product was isolated as described in Example 3 to afford the t-Boc-D-serine amide intermediate as a residue. The residue was dissolved in 40 ml methylene chloride, 12 ml trifluoroacetic acid (d=1.480) was added and the mixture was stirred at room temperature for three hours. The reaction mixture was made alkaline with 40% sodium hydroxide solution, the organic layer separated, the aqueous layer was saturated with sodium chloride and extracted with methylene chloride. The combined extracts were dried (MgSO₄) and concentrated to dryness in vacuo to yield the D-serine amide intermediate, free base.

C. 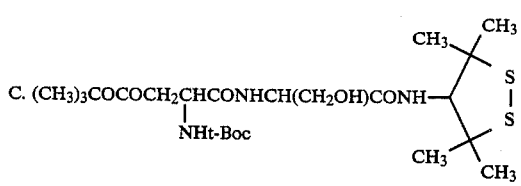

A mixture of 2.3 g (8.0 mmole) beta-t-butyl N-t-butoxycarbonyl-L-asparate, 0.88 ml (8.0 mmole) N-methylmorpholine and 0.77 ml (8.0 mmole) ethyl chloroformate in 40 ml methylene chloride was stirred at −12° C. for five minutes. A solution of 2.11 g (8.0 mmole) D-serine N-(3,3,5,5-tetramethyl-1,2-dithiolan-4y)amide 5 ml of the same solvent was added and stirring continued at −12° to −10° C. for ten minutes. The mixture was allowed to warm to room temperature, stirred for one hour at this temperature and the solvent evaporated. The residue was taken up in ethyl acetate, washed with dilute hydrochloric acid, sodium bicarbonate solution, brine, dried (MgSO₄) and the ethyl acetate evaporated to afford the desired product which was used in the next step. D. A solution of 2.6 g (4.78 mmole) of the product obtained in Part C, above, in 60 ml chloroform was fitted with a gas inlet tube and anhydrous hydrogen chloride bubbled through the solution. After five minutes, precipitation of solid was observed. The hydrogen chloride addition was continued for ten minutes, then the mixture was stirred at ambient temperature for one hour and evaporated to dryness in vacuo. The residue was taken up in water, washed with chloroform, the pH adjusted to 5.6, washed again with chloroform, and the aqueous phase evaporated in vacuo. Ethanol was added to the residue and the mixture evaporated to dryness in vacuo. The product was purified by recrystallization to obtain the title sweetener compound.

EXAMPLE 10

Employing the corresponding starting D-amino acid and the appropriate amine of formula

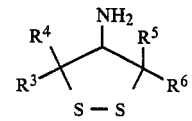

where $R^3$, $R^4$, $R^5$ and $R^6$ are as previously defined, in the above procedures likewise provides the L-D-compounds of formula (I)

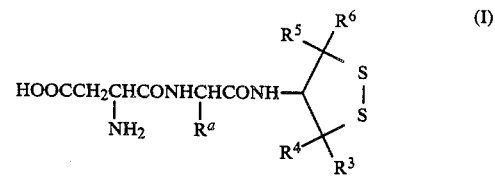

In any of the above procedures use o DL-aspartic acid and/or DL-amino acids, of the formula

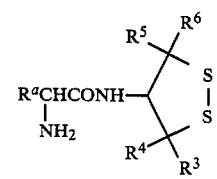

also provide the corresponding DL-D or DL-DL compounds of formula (I).

| $R^a$ | $R^3$ | $R^4$ | $R^5$ | $R^6$ |
|---|---|---|---|---|
| CH₃ | CH₃ | H | H | H |
| CH₃ | C₂H₅ | H | H | H |
| CH₃ | i-C₃H₇ | H | i-C₃H₇ | H |
| CH₃ | t-C₄H₉ | H | CH₃ | CH₃ |
| C₂H₅ | C₂H₅ | C₂H₅ | H | H |
| C₂H₅ | CH₃ | CH₃ | C₂H₅ | C₂H₅ |
| C₂H₅ | n-C₃H₇ | H | H | H |
| C₂H₅ | C₂H₅ | H | C₂H₅ | H |
| n-C₃H₇ | CH₃ | CH₃ | CH₃ | CH₃ |
| n-C₃H₇ | CH₃ | H | CH₃ | H |
| i-C₃H₇ | i-C₃H₇ | H | H | H |
| i-C₃H₇ | t-C₄H₉ | H | H | H |

EXAMPLE 11

Carbonated Cola Beverage

A carbonated cola beverage was prepared according to the composition given below. The resulting beverage was judged to have sweetness intensity comparable to a control beverage containing 11% sucrose.

| Ingredient | %, weight |
|---|---|
| Caffeine (1% aqueous solution) | 0.700 |
| L-Aspartyl-D-alanine N(cis, trans-2,6-dimethylcyclohexyl)amide (10% aqueous) | 0.180 |
| Cola flavor concentrate | 0.080 |
| Phosphoric acid (50% aqueous) | 0.040 |
| Citric acid (50% aqueous) | 0.066 |
| Sodium citrate (25% aqueous) | 0.210 |
| Caramel color (25% aqueous) | 0.370 |
| Lemon oil extract | 0.012 |

| Ingredient | %, weight |
| --- | --- |
| Lime oil extract | 0.021 |
| Carbonated water (3.5 volumes carbon dioxide) | q.s. |
| | 100.000 |

Replacement of the L-aspartyl-D-alanine N-(cis,-trans-2,6-dimethylcyclohexyl)amide in the above formulation with 0.22% of 10% aqueous L-aspartyl-D-2-aminobutyric acid N-(dicyclopropylcarbinyl)amide or 1.10% of 10% aqueous L-aspartyl-D-valine N-(dicyclopropylcarbinyl)amide affords carbonated cola beverages of like quality.

Similarly, use of a sweetening amount of alpha L-aspartyl-3,3,5,5-tetramethyl-4-(1,2-dithiolanyl)-D-alanineamide in the above formulation gives a carbonated cola beverage of like quality.

EXAMPLE 12

Low calorie table sweeteners are prepared according to the following formulations:

A. A powder form of sweetener is prepared by blending the following ingredients.

| Ingredient | %, weight |
| --- | --- |
| L-Aspartyl-D-alanine N—(2,2,4,4-tetramethyl-thietan-3-yl)amide | 0.18 |
| Crystalline sorbitol | 49.76 |
| Dextrin (dextrose equivalent 10) | 50.00 |
| Monosodium glutamate | 0.02 |
| Glucono-delta-lactone | 0.02 |
| Sodium citrate | 0.02 |
| | 100.00 |

One gram of the resulting blend is equivalent in sweetness to about three grams of sucrose.

B. A table sweetener in liquid form is prepared as follows.

| Ingredient | %, weight |
| --- | --- |
| L-Aspartyl-D-alanine N—(dicyclopropylcarbinyl)amide | 0.10 |
| Water | 99.80 |
| Sodium benzoate | 0.10 |
| | 100.00 |

One gram of the resulting solution is equivalent in sweetness to about 1.2 grams of crystalline sucrose. Use of alpha L-aspartyl-3,3,5,5-tetramethyl-4-(1,2-dithiolanyl)-D-alanineamide as sweetener in the appropriate amount in the above formulations also affords a suitable table sweetener.

PREPARATION A

2,4-Dibromo-2,4-dimethylpentan-3-one

To 136 g (1.2 mole) of diisopropylketone was added 2 ml of phosphorus tribromide and the mixture cooled to 10° C. To this was added dropwise 384 g (2.4 mole) of bromine, the mixture allowed to warm to room temperature. After two hours at this temperature the mixture was warmed at 55°–60° C. for one hour, then cooled and partitioned between chloroform and water. The water was discarded and the organic layer washed with sodium carbonate solution until neutral. The organic layer was dried ($MgSO_4$) and solvent evaporated to obtain 316 g (97%) of the desired product.

In like manner, bromination of the appropriate etone by the above procedure gave the following dibromoketones:

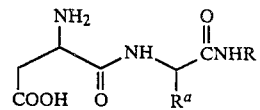

| $R^3$ | $R^4$ | $R^5$ | $R^6$ |
| --- | --- | --- | --- |
| $CH_3$ | H | $CH_3$ | H |
| $CH_3$ | H | H | H |
| $C_2H_5$ | H | H | H |
| $i\text{-}C_3H_7$ | H | H | H |
| $C_2H_5$ | H | $C_2H_5$ | H |
| $i\text{-}C_3H_7$ | H | $i\text{-}C_3H_7$ | H |
| $i\text{-}C_3H_7$ | H | $C_2H_5$ | H |
| $t\text{-}C_4H_9$ | H | $CH_3$ | $CH_3$ |
| $C_2H_5$ | $C_2H_5$ | $CH_3$ | $CH_3$ |
| $C_2H_5$ | $CH_3$ | $C_2H_5$ | $CH_3$ |

We claim:

1. An L-aspartyl-D-amino acid dipeptide amide of the formula

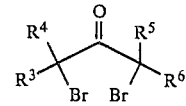

and the physiologically acceptable cationic and acid addition salts thereof, wherein $R^a$ is methyl, hydroxymethyl, ethyl, n-propyl or isopropyl and R is

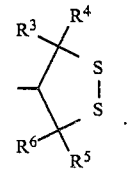

where at least one of $R^3$, $R^4$, $R^5$ and $R^6$ is alkyl having from one to four carbon atoms, the remainder are hydrogen or alkyl having from one to four carbon atoms, the sum of the carbon atoms in $R^3$, $R^4$, $R^5$ and $R^6$ is not greater than six; and when both of $R^3$ and $R^4$ or $R^5$ and $R^6$ are alkyl, they are methyl or ethyl.

2. A compound according to claim 1 wherein $R^a$ is methyl.

3. A compound according to claim 1 whrein R is

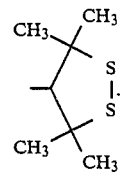

4. The compound according to claim 3: alpha-L-aspartyl-N-(3, 3,5,5-tetramethyl-4-1,2-dithiolanyl)-D-alanineamide.

5. A composition for sweetening edible materials which comprises a sweetening amount of a compound according to claim 1 and a non-toxic carrier.

6. A composition according to claim 5 wherein said compound is alpha-L-aspartyl-N-(3,3,5,5-tetramethyl-4-1,2-dithiolanyl)-D-alanineamide.

7. A sweetened edible composition which comprises an edible material and a sweetening amount of a compound according to claim 1.

8. A sweetened edible composition according to claim 7 wherein said compound is alpha-L-aspartyl-N-(3,3,5,5-tetrametyl-4-1,2-dithiolanyl)-D-alanineamide.

9. A sweetened edible composition according to claim 7 wherein said edible material is a carbonated beverage.

10. A sweetened edible composition according to claim 8 wherein said edible composition is a carbonated beverage.

11. A method for sweetening edible materials which comprises adding thereto a sweetening amount of a compound according to claim 1.

12. A method according to claim 11 wherein said compound is alpha-L-aspartyl-N-(3,3,5,5-tetramethyl-4-1, 2-dithiolanyl)-D-alanineamide.

* * * * *